(12) United States Patent
Kwalwasser et al.

(10) Patent No.: US 12,702,345 B2
(45) Date of Patent: Aug. 11, 2026

(54) BRAIN STATE OPTIMIZATION WITH AUDIO STIMULI

(71) Applicant: Arctop LTD, Tel Aviv-Jaffa (IL)

(72) Inventors: Eitan Kwalwasser, Tel Aviv (IL); Daniel Furman, San Francisco, CA (US)

(73) Assignee: Arctop LTD, Tel Aviv-Jaffa (IL)

( * ) Notice: Subject to any disclaimer, the term of this patent is extended or adjusted under 35 U.S.C. 154(b) by 607 days.

(21) Appl. No.: 17/928,242

(22) PCT Filed: May 26, 2021

(86) PCT No.: PCT/US2021/034354
§ 371 (c)(1),
(2) Date: Nov. 28, 2022

(87) PCT Pub. No.: WO2021/242927
PCT Pub. Date: Dec. 2, 2021

(65) Prior Publication Data

US 2023/0218221 A1 Jul. 13, 2023

Related U.S. Application Data

(60) Provisional application No. 63/170,114, filed on Apr. 2, 2021, provisional application No. 63/030,126, filed on May 26, 2020.

(51) Int. Cl.
*A61B 5/375* (2021.01)
*A61B 5/00* (2006.01)
(Continued)

(52) U.S. Cl.
CPC ............ *A61B 5/375* (2021.01); *A61B 5/0205* (2013.01); *A61B 5/372* (2021.01); *A61B 5/38* (2021.01);
(Continued)

(58) Field of Classification Search
CPC ........ G16H 20/70; G06V 40/18; G06N 20/00; G06N 5/01; G06N 3/09; G06N 3/04;
(Continued)

(56) References Cited

U.S. PATENT DOCUMENTS 11,307,650 B1 * 4/2022 Guerra Filho ......... G06V 40/18
12,093,457 B2 * 9/2024 Yildiz ...................... G09B 5/06
(Continued)

FOREIGN PATENT DOCUMENTS

WO WO 2019/104008 A1 5/2019
WO WO 2020/086959 A1 4/2020

OTHER PUBLICATIONS

PCT International Search Report and Written Opinion, International Application No. PCT/US2021/034354, dated Oct. 5, 2021, 12 Pages.
(Continued)

*Primary Examiner* — Mihir K Rayan
(74) *Attorney, Agent, or Firm* — Fenwick & West LLP

(57) ABSTRACT

A method and system for generating an optimal audio stimulus for achieving a target brain state value for a brain state. The method and system can be used to generate one or more brain state models which can decode brain activity signals to predict brain state values. The brain state models can be applied to brain activity signals captured while users are performing tasks with an audio stimulus. Audio features of the audio stimulus can be extracted. An audio-brain model can be trained on the predicted brain state values and the audio features. From the trained audio-brain model, the optimal audio stimulus can be generated.

11 Claims, 10 Drawing Sheets

(51) Int. Cl.

| | |
|---|---|
| ***A61B 5/0205*** | (2006.01) |
| ***A61B 5/372*** | (2021.01) |
| ***A61B 5/38*** | (2021.01) |
| ***G06N 3/004*** | (2023.01) |
| ***G16H 20/70*** | (2018.01) |

(52) U.S. Cl.
CPC .......... *A61B 5/7267* (2013.01); *A61B 5/7275* (2013.01); *G16H 20/70* (2018.01); *A61B 5/6803* (2013.01); *G06N 3/004* (2013.01)

(58) Field of Classification Search
CPC .... G06N 3/004; A61B 5/7275; A61B 5/7276; A61B 5/6803; A61B 5/4836; A61B 5/38; A61B 5/375; A61B 5/372; A61B 5/165; A61B 5/0205
See application file for complete search history.

(56) References Cited

U.S. PATENT DOCUMENTS

| | | | | |
|---|---|---|---|---|
| 2004/0230105 | A1* | 11/2004 | Geva | A61B 5/316 600/509 |
| 2010/0324440 | A1* | 12/2010 | Moore | A61B 5/377 600/544 |
| 2015/0351655 | A1 | 12/2015 | Coleman | |
| 2016/0022168 | A1 | 1/2016 | Luczak et al. | |
| 2016/0267809 | A1 | 9/2016 | Decharms et al. | |
| 2017/0339484 | A1 | 11/2017 | Kim | |
| 2019/0246936 | A1 | 8/2019 | Garten et al. | |
| 2019/0269345 | A1* | 9/2019 | Sriram | A61M 21/00 |
| 2021/0390366 | A1 | 12/2021 | Furman et al. | |

OTHER PUBLICATIONS

Matsumoto et al., "Auditory Steady-State Response Stimuli based BCI Application—The Optimization of the Stimuli Types and lengths", arvix.org, Oct. 10, 2012, retrieved on [Aug. 22, 2021]. Retrieved from the internet <URL: https://arxiv.org/pdf/1210.2943.pdf> entire document.

Bhatti, A. et al., "Human emotion recognition and analysis in response to audio music using brain signals," Computers in Human Behavior, vol. 65, Dec. 2016, pp. 267-275.

European Patent Office, Partial Supplementary European Search Report, EP Patent Application No. 21812693.6, Oct. 15, 2024, 18 pages.

European Patent Office, Extended European Search Report, EP Patent Application No. 21812693.6, Jan. 10, 2025, 16 pages.

Sarkar, R. et al., "Recognition of emotion in music based on deep convolutional neural network," Multimedia Tools and Applications, vol. 79, Sep. 13, 2019, pp. 765-783.

* cited by examiner

BRAIN STATE OPTIMIZATION WITH AUDIO STIMULI

CROSS REFERENCE TO RELATED APPLICATIONS

This application claims the benefit of U.S. Provisional Application No. 63/030,126 filed on May 26, 2020, and U.S. Provisional Application No. 63/170,114 filed on Apr. 2, 2021, both of which are incorporated by reference in their entirety.

BACKGROUND

The present disclosure generally relates to neural signal processing, and specifically to a system and method for providing stimuli to achieve a target brain state using decoded brain activity.

It is well studied that certain stimuli (e.g., auditory stimuli, visual stimuli, olfactory stimuli, etc.) and arrangements of stimuli (e.g., music, sound effects, video, etc.) can be pleasant, reduce stress, increase motivation, and more. Certain stimuli can, of course, do the opposite as well. In examples, many scientific studies have explored the relationship between sound, music and humans from an objective perspective that seek to analyze properties of audio that correlate with specific emotions or particular attentional response in humans. However, sound perception is largely subjective to the users and application of providing sound and/or other types of stimuli to achieve desired brain states in a personalized manner have been largely unrealized.

SUMMARY

Provision of an optimal stimulus helps to optimize a user's brain state. The method(s) and system(s) herein describe principles to decoding human brain activity and training models to predict a user's brain state value for a particular brain state based on a brain activity signal. Further, the method(s) and system(s) provide for identifying informative stimulus features that contribute significantly to the human brain state. These informative stimulus features can be used to generate an optimal stimulus.

In specific applications, the method(s) and system(s) can be adapted to achieve desired states of flow (e.g., a combination of focus and enjoyment) during performance of a task (e.g., work-related task, training-related task, learning-related task, skill-building-related task, etc.) in a suitable environment (e.g., office space, home working space, school environment, training environment, etc.). States of flow can be promoted, using the system(s) and method(s), for individual users and/or groups of users according to embodiments, variations, and examples of the inventions.

In one or more embodiments, method(s) and system(s) for generating an optimal audio stimulus (and/or other stimulus) for achieving a target brain state value for a brain state are disclosed. The method and system can be used to generate one or more brain state models which can decode brain activity signals to predict brain state values. In examples pertaining to audio stimuli, the brain state models can be applied to brain activity signals captured while users are performing tasks with an audio stimulus. Audio features of the audio stimulus can be extracted. An audio-brain model can be trained on the predicted brain state values and the audio features. From the trained audio-brain model, the optimal audio stimulus can be generated. Additional variations are covered in detail further below.

The optimal audio stimulus for brain state optimization may be used in a variety of contexts. In one or more contexts, the audio stimulus can be provided to digital music streaming platforms for use by their users to optimize brain state. In another context, the audio stimulus can be used in digital health. In still other contexts, the audio stimulus can be used in conjunction with other content (e.g., in a virtual reality (VR) environment, at a sporting event, in a movie theater, at a concert, etc.).

The principles discussed above can be applied to other types of stimuli, such as visual or haptic. Additionally, the method(s) and system(s) can generate optimal combinations of such stimuli to create an optimal brain state. Moreover, the method(s) and system(s) can optimize for multiple different brain states, e.g., maximizing a focus state and minimizing an entrancement state.

The system(s) and method(s) described herein can be adapted to be used by a user who is remote from a research or clinical environment, where the user is moving about in his or her daily life. The method(s) and/or system(s) can thus be provided to enhance user experiences with content provided in an augmented reality setting and/or virtual reality setting.

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION

1. System Environment

Figure 1:
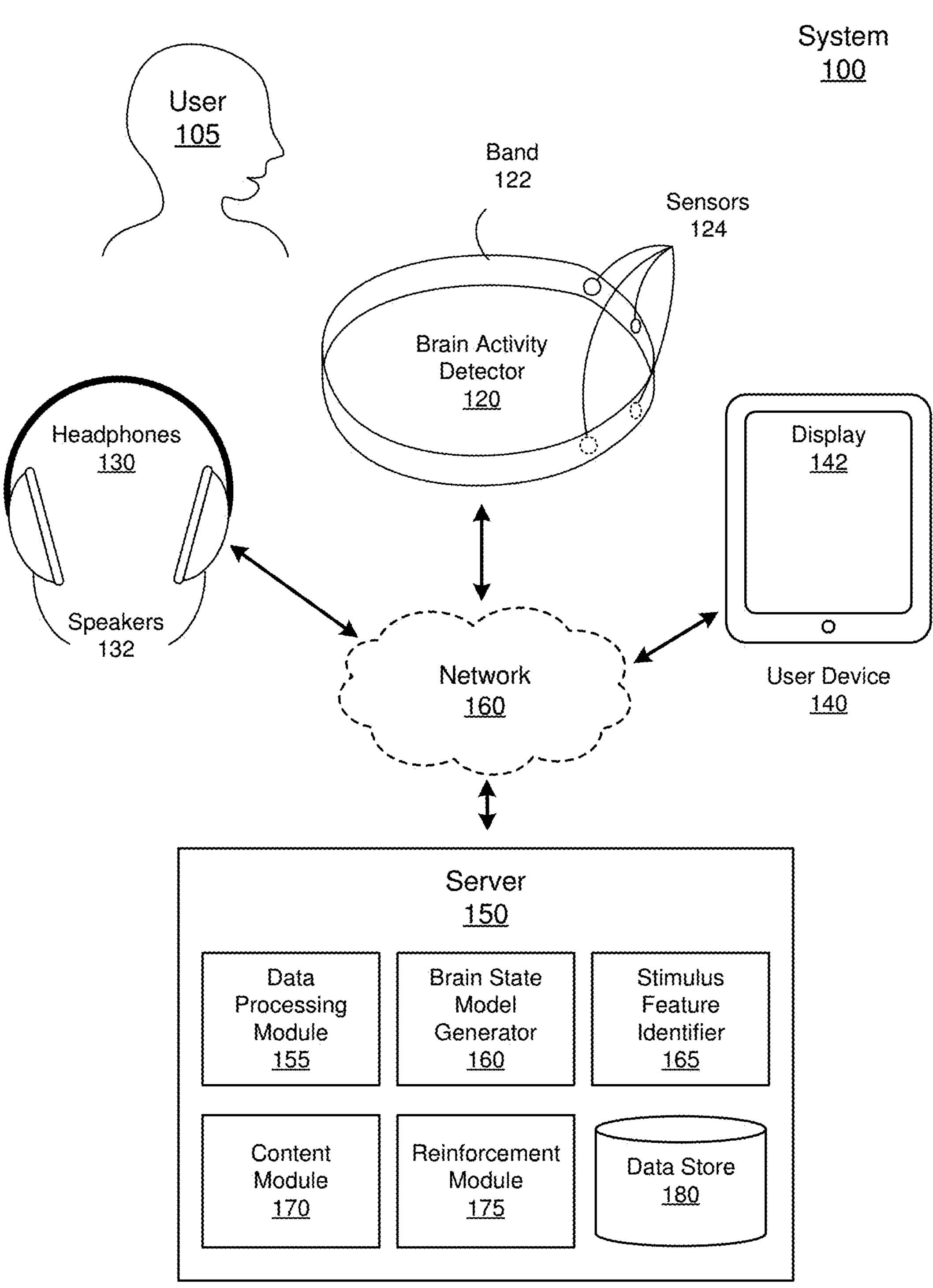
FIG. 1 depicts a system environment of a system for digital content delivery for brain state optimization, in accordance with one or more embodiments.

FIG. 1 depicts a system environment of a system 100 for digital content delivery for brain state optimization, in accordance with one or more embodiments. The system 100 includes a brain activity detector 120, headphones 130, a user device 140, a server 150, and a network 160. The brain activity detector 120 is configured to measure brain activity of a user 105 with sensors 124 that are placed against the skin of the user 105, for example, electroencephalography (EEG) sensors placed on the forehead. The headphones 130 are configured to provide audio stimuli to a user 105 via one or more speakers 132. The user device 140 is configured to run an application (or website, etc.) with which the user 105 may perform one or more tasks and may provide responses to one or more surveys. The server 150 collects data recorded by the brain activity detector 120 and the user device 140. The server 150 also generates and/or provides the audio stimuli to be played by the headphones 130. In addition, the server 150 analyzes the brain activity signal captured by the brain activity detector 120 to identify informative features (e.g., audio features) that have an effect on brain state. The server 150 can generate or adjust the stimuli (e.g., audio stimuli) based on the identified informative audio features to optimize a user's brain state.

The brain activity detector 120 is configured to measure brain activity of the user 105. The brain activity detector 120 comprises a band 122 and the sensors 124 coupled to the band 122. The band 122 is worn around the head of the user 105. When worn, the sensors 124 are coupled to the user 105, e.g., against the forehead of the user 105. The band 122 may have various designs. Such designs can include a cap or covering over part of the head of the user 105, or it may only attach to the forehead of the user without wrapping around the head (e.g., via an adhesive or by attachment to an item wearable by the user, such as a hat or glasses of the user 105). The sensors 124 could also be individually adhered to the user's head or to an item wearable by the user. In one embodiment, the set of sensors 221 includes electrodes for electrical surface signal (e.g., electroencephalogram (EEG) signal, electrocorticography (ECoG) signal, etc.) generation, where the set of sensors 221 can include one or more of electrolyte-treated porous materials, polymer materials, fabric materials, or other materials that can form an electrical interface with a head region of a user. In alternative embodiments, the set of sensors 221 can include sensors operable for one or more of: magnetoencephalography (MEG), positron emission tomography (PET), functional magnetic resonance imaging (fMRI), single neuron signal sensing (e.g., using neurotrophic electrodes, using multi-unit arrays), and other neurosensing modalities. In still alternative embodiments, the set of sensors 221 can include sensors operable for optical neurosensing modalities including one or more of: diffuse optical tomography (DOT), near-infrared spectroscopy (fNIRS), functional time-domain near-infrared spectroscopy (TD-fNIRS), diffuse correlation spectroscopy (DCS), speckle contrast optical tomography (SCOT), time-domain interferometric near-infrared spectroscopy (TD-iNIRS), hyperspectral imaging, polarization-sensitive speckle tomography (PSST), spectral decorrelation, and other imaging modalities.

The headphones 130 are configured to provide audio stimuli to the user 105. The headphones 130 comprise at least one or more speakers 132 for providing the audio stimuli to the user 105. In other embodiments, other audio output devices may be implemented, e.g., speakers, earphones, etc. Various different designs for the headphones 130 may be used.

The user device 140 is configured to run an application with which the user 105 may perform one or more tasks and may provide responses to one or more surveys. The user device 140 is a general computing device, such as a laptop, a tablet, a mobile phone, etc. A general computing device includes at least one computer processor and one or more storage media storing computer-readable instructions for instructing the processor to perform operations. The general computing device may further include input devices, output devices, wireless transmitters, displays, etc. The user device 140 comprises (among other general computing components) a display 142, which provides visual content to the user 105. Visual content may include tasks for the user 105 or visual stimuli that affects a user's brain state. In addition, the display 142 may be a touchscreen display that can receive user input. As such, the user device 140 can prompt the user 105 to perform tasks such as playing a game, solving puzzles, typing, etc. The user device 140 can also provide surveys to the user 105 and record responses provided by the user 105 via the touchscreen. The user device 140 can use other input devices for recording responses by the user, e.g., an audio microphone can record a user providing a vocal response.

Additional sensors can be included in the brain activity detector 120, the headphones 130, and/or the user device 140. The additional sensors may include audio sensors (e.g., directional microphones, omnidirectional microphones, etc.) to process captured audio associated with a user's interactions with the digital content and/or environments surrounding the user. Sensors can additionally or alternatively include optical sensors (e.g., integrated with cameras) to process captured optically-derived information (associated any portion of an electromagnetic spectrum) associated with a user's interactions with the digital content and/or environments surrounding the user. Sensors can additionally or alternatively include motion sensors (e.g., inertial measurement units, accelerometers, gyroscopes, etc.) to process captured motion data associated with a user's interactions with the digital content and/or environments surrounding the user. Sensors can additionally or alternatively include biometric monitoring sensors including one or more of: skin conductance/galvanic skin response (GSR) sensors, sensors for detecting cardiovascular parameters (e.g., radar-based sensors, photoplethysmography sensors, electrocardiogram sensors, sphygmomanometers, etc.), sensors for detecting respiratory parameters (e.g., plethysmography sensors, audio sensors, etc.), body temperature sensors, and/or any other suitable biometric sensors. As such, additional sensor signals can be used by the server 150 for extraction of non-brain activity states (e.g., auxiliary biometric signals, auxiliary data, contextual data, etc.) that are relevant to determining user states. For instance, environmental factors (e.g., an analysis of environmental threats) and/or devices states (e.g., a user's device is wirelessly connected or connected otherwise to a network) can be used as inputs. The system 100 can thus process outputs of the sensors to extract features useful for guiding content modulation in near-real time according to the method(s) described below.

The server 150 analyzes data recorded by the brain activity detector 120 and the user device 140 to optimize the audio stimuli provided to the headphones 130 (e.g., in relation promoting, maintaining, and/or otherwise achieving desired states of flow for individual users and/or groups of users). In embodiments with visual stimuli or a combination of audio and visual stimuli, the server 150 optimizes accordingly. The server 150 is a general computing device. The server 150 includes a data processing module 155, a brain state model generator 160, a feature identifier 165, a content module 170, a reinforcement module 175, and a data store 180.

The data processing module 155 receives and processes data received by the server 150. The data received includes brain activity data recorded by the brain activity detector 120 and inputs by the user 105 via the user device 140. The data may include other biological data, such as, heart rate, blood pressure, electrocardiography data, body temperature, motion data, other biometric data, etc. The data is processed by the data processing module 155, which may include, but is not limited to, noise removal, filtering, data partitioning, labeling, etc. In one embodiment with an EEG signal, the data processing module 155 applies, to each EEG channel, a band-pass filter of 0.5-70 Hz with a notch filter of 60 Hz to remove noise. The data processing module 155 then uses a sliding window with a stride of 200 ms (5 Hz) to partition each EEG channel into 5 second epochs.

The brain state model generator 160 generates one or more brain state models based on the brain activity data and the user survey responses. The user survey responses report a value for a particular brain state. In embodiments, the different brain states analyzed can include one or more of: an alertness state (e.g., a sleep state, alertness level), a state of focus (e.g., focused, distracted, etc.), an emotional state (e.g., happy, angry, sad, bored, scared, calm, confused, surprised, etc.), a mental health state (e.g., a state of anxiety, a state of depression, a state characterized in a manual of mental health conditions, etc.), a neurological health state (e.g. seizure, migraine, stroke, dementia, etc.), a state of sobriety, a state of overt/covert attention, a state of reaction to sensory stimuli, a state of spatial orientation, a state of cognitive load (e.g. of being overloaded), a state of flow, a state of entrancement, a state of imagery (e.g. of motor action, of visual scenes, of sounds, of procedures, etc.), a memory function state (e.g. encoding effectively, forgetting, etc.), and/or any other suitable brain activity state. The brain state model generator 160 extracts features for the brain activity data. The features may include power spectrum features (e.g., average power in different frequency bands), power spectrum interactions (e.g., the power spectrum ratio between bands and engagement index), time domain features (e.g., first four moments, entropy, and number of zero-crossing points), pairwise correlations between channels. In variations, individual features, such as focus-associated features and enjoyment-associated features, extracted from the neurological data, can be combined for determination of derivative brain states (e.g., states of flow), which can be used to increase or optimize output or performance by one or more users in a particular environment (e.g., work environment, school environment, home environment, training environment, etc.).

Embodiments, variations, and examples of systems and methods for extraction of brain state features from brain signal data are described in U.S. application Ser. No. 16/762,262 filed on Nov. 20, 2021, and U.S. application Ser. No. 17/285,082 filed on Oct. 25, 2019, which are each incorporated herein in its entirety by this reference.

The brain state model generator 160 trains one or more brain state models based on the extracted features from the brain activity signal and the user survey responses. In one embodiment, the brain state models are random forest regression models. In other embodiments, the brain state models utilize different machine learning techniques, e.g., neural networks, multinomial regressors, other decision trees, etc. The trained brain state models are configured to predict a value for the brain state (or the brain state value over time) based on an input brain activity signal. The brain state models may be stored in the data store 180. For a given user, the server 150 may select a brain state model that best fits the user's survey responses and brain activity data. The best fit model provides the closest prediction of the user's brain state value based on the brain activity data. The selected brain state model may be stored in a user profile for that user, such that the server 150 may provide tailored content to each user.

The stimulus feature identifier 165 identifies informative stimulus features that affect a user's brain state. The stimulus feature identifier 165 extracts features for a stimulus provided to the user 105 associated with the recorded brain activity data. Each type of stimulus may use any of the formats used for that type of stimulus. For example, audio stimuli can be formatted as WAV, AIFF, AU, FLAC, Monkey's Audio, WavPack, TTA, ATRAC, MPEG-4, MP3, Opus, Vorbis, WMA lossy, or etc. For example, a musical soundscape was provided as an audio stimulus to the user 105 as the user 105 performed a task. The stimulus feature identifier 165 extracts audio features from the audio stimulus using a sliding window (e.g., 25 ms). Audio features may include, but are not limited to, energy, spectral entropy, chroma coefficients, etc. The stimulus feature identifier 165 may perform a dimensionality reduction on the audio features, e.g., principal component analysis (PCA). The stimulus feature identifier 165 trains an audio-brain regression model with the audio features and the predicted brain state values (based on the brain state models). The trained audio-brain regression model predicts a brain state value based on audio features present in an audio stimulus. From the trained audio-brain regression model, the stimulus feature identifier 165 can extract informative audio features that contribute significantly to predicting brain state value. The principles can be applied similarly to other forms of stimuli, e.g., visual stimuli, or for predicting other brain states (different from the focus state). The informative stimulus features and the trained audio-brain regression model may be stored in the data store 180. In some embodiments, the stimulus feature identifier 165 may identify features specific to an individual, based on the best fit brain state model for that individual.

The content module 170 generates and selects digital content to be presented to the user 105. The content module 170 may generate digital content to optimize a user's brain state based on the identified informative stimulus features. For example, the content module 170 considers the informative audio stimulus features to generate an audio stimulus to maximize a user's focus state. In other embodiments, the content module 170 may generate digital content (e.g., audio content, visual content, etc.) to minimize one or more brain states, to maximize one or more other brain states, or some combination thereof. Additionally or alternatively, the content module 170 can generate or provide instructions for generating other stimuli (e.g., temperature stimuli, olfactory stimuli, etc.) for adjusting environmental parameters of users in order to achieve desired brain states. In embodiments including audio stimuli, the content module 170 provides the generated digital content to the headphones 130 for presentation to the user 105. As such, the content module 170 can include architecture with interfaces (e.g., wired interfaces, wireless interfaces) to environmental control devices associated with environments of users, in order to promote achievement of desired brain states.

The reinforcement module 175 collects additional brain activity data associated with the user 105 experiencing the digital content provided by the content module 170. The reinforcement module 175 may apply the trained brain state models to the brain activity data associated with the digital content to determine a brain state value of the user while experiencing the digital content. The reinforcement module 175 may calculate a loss between the predicted brain state value based on the trained audio-brain regression model and the user's determined brain state value. The reinforcement module 175 may toggle stimulus features of the digital content to minimize the loss.

The data store 180 stores some or all of the data used by the components of the system 100. The data stored may include biological data recorded by the sensors 124, digital content created by the content module 170, survey responses by the user, user profiles including a specific brain state model and/or stimulus features specific to each user, etc.

The components of the system 100 can be configured to communicate with the through network 160. The network 160 can include any combination of local area and/or wide area networks, using both wired and/or wireless communication systems. In one embodiment, the components of the system 100 use standard communications technologies and/or protocols. For example, the network 160 includes communication links using technologies such as Ethernet, IEEE 802.11, worldwide interoperability for microwave access (WiMAX), 3G, 4G, 5G, code division multiple access (CDMA), global system for mobile communications (GSM), digital subscriber line (DSL), etc. Examples of networking protocols used for systems communication include transmission control protocol/Internet protocol (TCP/IP), hypertext transport protocol (HTTP), WebSocket (WS), and file transfer protocol (FTP). In some embodiments, all or some of the communication links of components of the system 200 may be encrypted using the secure extension of said protocol such as hypertext transfer protocol over secure sockets layer (SSL), WebSocket secure (WSS), secure file transfer program (SFTP) or any other suitable technique or techniques.

In one or more embodiments, the various components of the system 100 may be variably integrated. For example, the brain activity detector 120 can be integrated with the headphone 130 to form a single device that is worn by the user 105. In other embodiments, the stimuli generated by the system 100 may be provided to one or more other output devices, e.g., another audio speaker, a different electronic display device, another head-mounted display, etc. As another example, the display 142 of the user device may be integrated into eyeglasses and mounted with the headphones in a head-mounted display (HMD), examples of which are shown in FIGS. 2A and 2B.

Figure 2A:
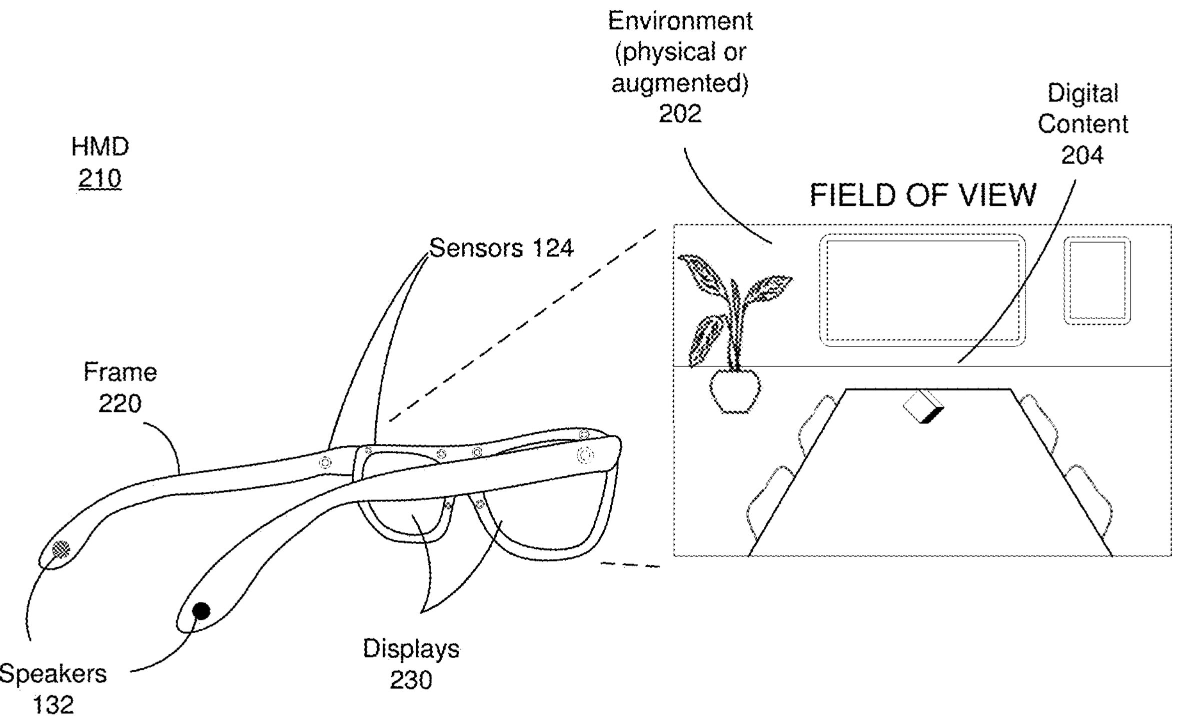
FIG. 2A shows a HMD, in accordance with one or more embodiments.

FIG. 2A shows a HMD 210, in accordance with one or more embodiments. The HMD 210 is configured to be worn by a user and to deliver digital content, e.g., generated by the server 150. The HMD 210 shown in FIG. 2A is formed as an eyewear device. The HMD 210 comprises a frame 220 which supports two displays 230 formed in the shape of eyeglasses. The displays 230 may be at least partially transparent to allow light from the environment 202 to reach the user's eyes. The displays 230 may provide additional digital object 204 to augment the light from the environment 202, thereby providing augmented reality. The displays 230 may provide for the same functionality as described for the display 142, e.g., providing user surveys, displaying tasks, etc. The frame 220 also supports the sensors 124 which couple to the user to record brain activity data and the speakers 132 for providing audio content to the user. The HMD 210 can provide audio stimuli, visual stimuli, or a combination thereof to the user.

Figure 2B:
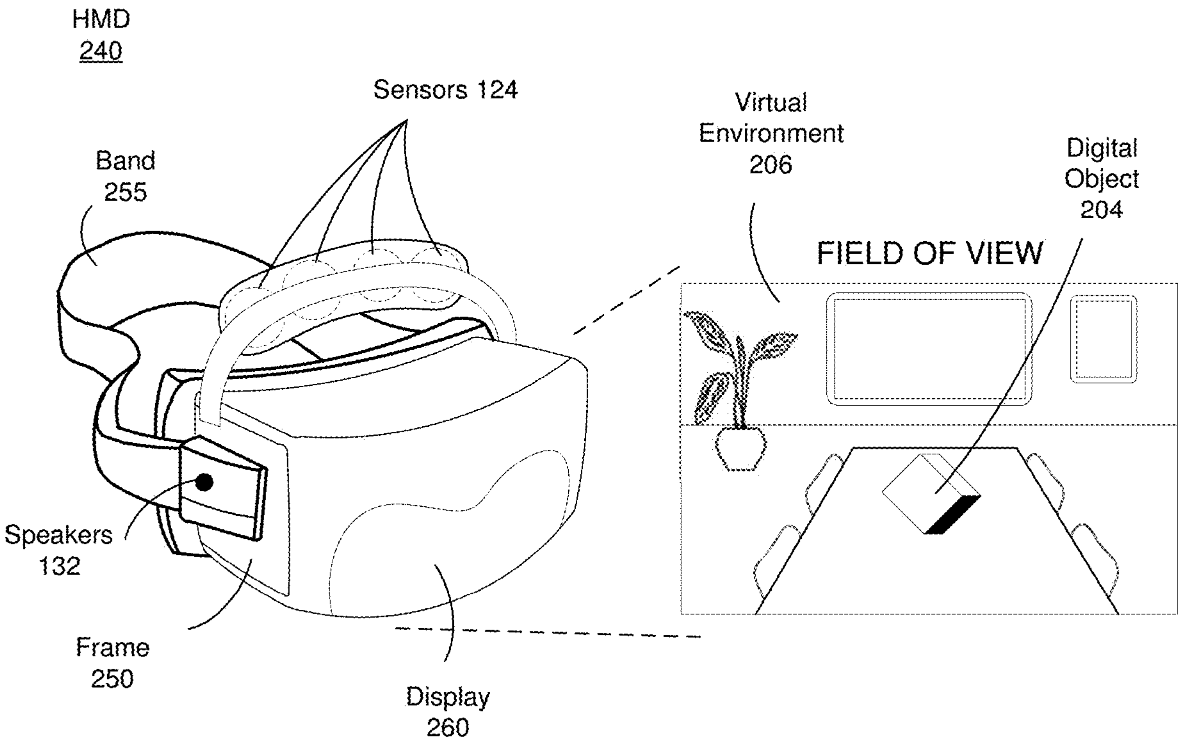
FIG. 2B shows a HMD, in accordance with one or more embodiments.

FIG. 2B shows a HMD 240, in accordance with one or more embodiments. The HMD 240 is configured to be worn by a user and to deliver digital content, e.g., generated by the server 150. The HMD 240 shown in FIG. 2B is formed as an enclosed display that fits over the face of the user. The HMD 240 comprises a frame 250 that holds the enclosed display 260 and a band 255 that provides tension to hold the frame 250 against the user's face. The display 260 operates provides digital content to the user including the virtual environment 206 with digital object 204. The sensors 124 are placed on a support arm of the frame 250 which presses the sensor 124 against the forehead of the user. The speakers 132 (a right speaker shown with a left speaker occluded from view) provide audio content to the user. The HMD 240 can provide audio stimuli, visual stimuli, or a combination thereof to the user.

The HMDs 210 and/or 240 can additionally include one or more of: power management-associated devices (e.g., charging units, batteries, wired power interfaces, wireless power interfaces, etc.), fasteners that fasten wearable components to a user in a robust manner that allows the user to move about in his/her daily life, and any other suitable components. The HMDs 210 and/or 240 can also include interfaces with other computing devices, such as a mobile computing device (e.g., tablet, smartphone, smartwatch, etc.) that can receive inputs that contribute to control of content delivered through the HMDs 210 and/or 240, and/or deliver outputs associated with use of the HMDs 210 and/or 240 by the user. The HMDs 210 and/or 240 can further have other suitable form factors, including having a form factor that is attachable to a user's own glasses or other item wearable by a user (e.g., a cap).

2. Method—Brain State Optimization with Audio Stimulus

Figure 3:
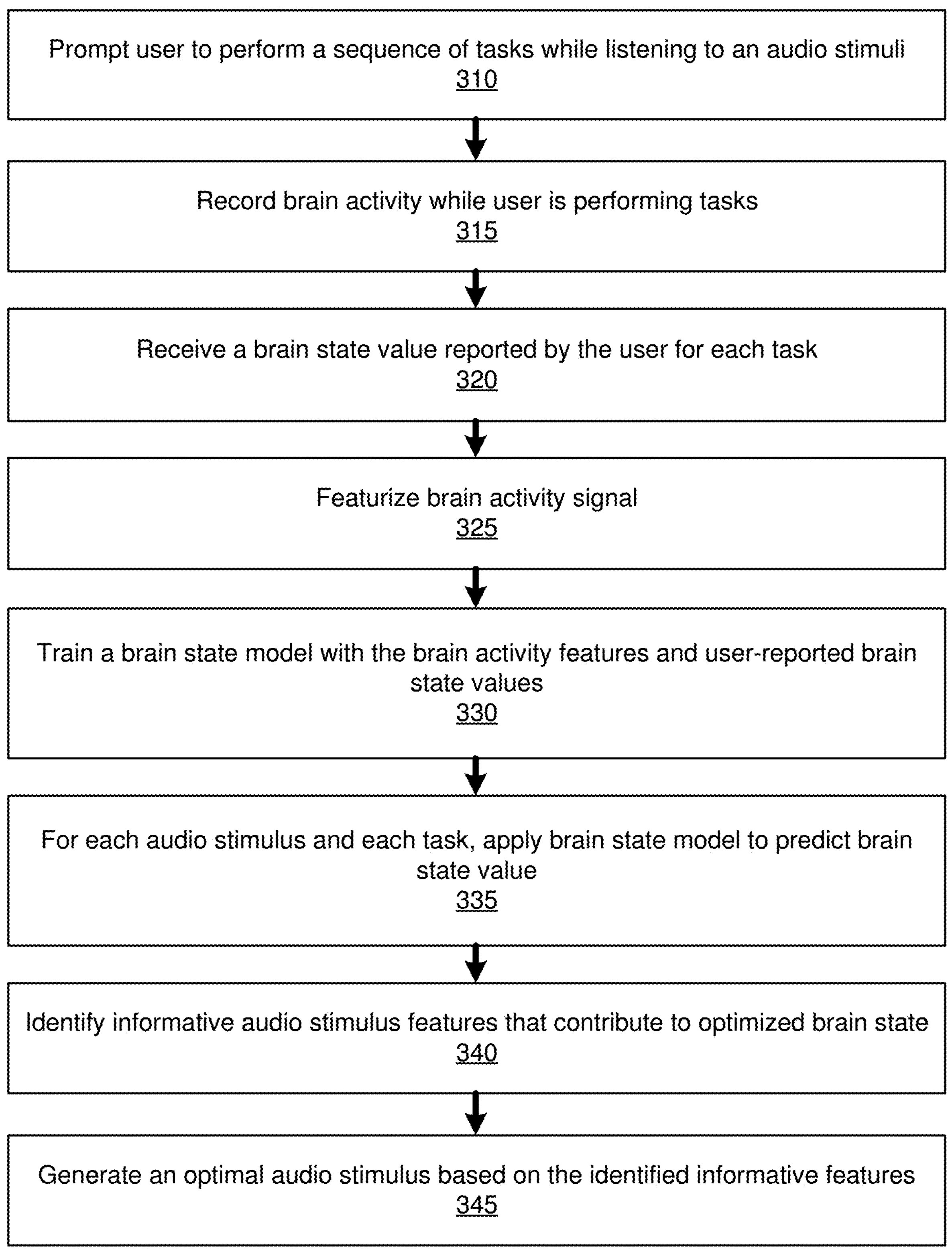
FIG. 3 is a flowchart illustrating a method of optimizing a user's brain state with an audio stimulus, in accordance with one or more embodiments.

FIG. 3 is a flowchart illustrating a method of optimizing a user's brain state with an audio stimulus, in accordance with one or more embodiments. The system 100 is described as performing the method; however, other devices described herein this disclosure may be used to perform any of the steps of the method.

The system 100 prompts 310 a user to perform a sequence of tasks while listening to an audio stimulus (e.g., to calibrate performance of the system and/or associated methods). The audio stimulus may be a previously generated playlist or soundscape on a music streaming platform. The sequence of tasks include at least two different tasks. Tasks can be divided into categories, wherein two different tasks are also selected from two different categories. For example, there can be 4 categories of tasks: arithmetic (e.g., solving mental math problems), creativity (e.g., a game called "Alternative Use" where the user provides as many uses of a given object), gaming (e.g., Tetris™), and a user-selected task. As a first example, the sequence of tasks may incorporate one arithmetic task and one gaming task. In another example, a creativity task, a user-selected task, and a gaming task are used. In another example, a sequence of tasks can be designed to achieve calibration in a desired manner (e.g., with improved efficiency), where the sequence includes a Tetris™/gaming task provided with a medium difficulty level, an arithmetic task provided with an easy difficulty level, a creativity task, a Tetris™/gaming task provided with a slow difficulty level, an arithmetic task provided with a hard difficulty level, and a Tetris' task provided with a fast difficulty level, where the sequence of tasks has a total duration of under 10 minutes. The system 100 prompts 310 the user to perform the sequence while providing the audio stimulus to the user, i.e., a test run. The system may 100 prompt the user to perform additional test runs with different audio stimuli, e.g., a different playlist or a different soundscape. A control run is also held where the user performs the sequence of tasks without any audio stimulus. The system 100 may repeat the method of a number of users to form a set of training data.

The system 100 records 315 the user's brain activity while the user is performing the sequence of tasks. As described above, the system 100 may include the brain activity detector 120 comprising sensors 124 for recording user brain activity. The system 100 records brain activity during the test run (or test runs) and the control run.

The system 100 receives 320 a brain state value for each task reported by the user. In one embodiment, the system 100 may provide a survey to the user (e.g., via the display 142 of the user device 140) asking the user to provide a value for their brain state during the task. For example, the survey question is "How focused did you feel while performing the previous Task?" The response input icon can request the user to enter a number 1-10, or toggle a slider ranging from "Not at all" to "Very", etc. The system 100 may prompt once at the end of each task or may prompt periodically throughout a task for greater granularity in response data.

The system 100 featurizes 325 brain activity signal. Prior to featurization, the system 100 may also process the recorded brain activity data (e.g., as described for the data processing module 155). The system 100 extracts features from the brain activity signal using a sliding window to partition the brain activity data into 5 second epochs. The sliding window sizing can be adjusted to create smaller or bigger sized epochs (e.g., less than 5 second epochs, greater than 5 second epochs).

The system 100 trains 330 a brain state model with the brain activity features. With a single user, the system 100 can train a single brain state model. With a set of users, the system 100 can train a plurality of brain state models based on randomly sampled subsets of users. In one embodiment, the brain state models are trained as a plurality of regression models by sampling random users to use as training data for each regression model. A trained brain state model is configured to receive a brain activity signal and to output a predicted brain state value (or the brain state value over time). For example, the trained brain state model can receive an EEG signal and output a user's focus state over time. The model(s) can be generated by iterative training over a period of time. Thus, the training 330 step may be an ongoing process that continues as the model(s) are applied. The system 100 can also apply model(s) that were previously trained, so the training steps of the method may not occur in that case.

The system 100, for each audio stimulus and each task, applies 335 one or more brain state models to predict brain state value. The system 100 decodes a user's brain state over time by applying one or more of the brain state models to the user's brain activity data. The system 100 may select which brain state model(s) to use based on which one best fits the user's self-reported brain state value while performing the tasks. The system 100 can also apply the brain state model(s) to the control run, providing a basis of comparison between the test runs and the control run.

The system 100 identifies 340 informative audio stimulus features that contribute to optimized brain state. The system 100 can seek to optimize brain state by maximizing, minimizing, or achieving a target value. The system 100 applies the brain state model(s) to the brain activity data of a plurality of users, defined as a training set of users. The system 100 also extracts audio features from each of the audio stimuli provided to the users associated with the brain activity data. The system 100 can use a sliding window to also partition the audio stimuli into audio epochs. The system 100 can train a regression model between the extracted audio features and the predicted brain state. From the regression model, the system 100 extracts the informative audio features. Other machine learning algorithms may be used in place of the regression model.

The system 100 generates 345 an optimal audio stimulus based on the identified informative features. Based on the identified informative features, the system 100 can generate the optimal audio stimulus by toggling the audio features of the audio stimulus to achieve an optimal brain state. In other embodiments, the system 100 adjusts a previously generated audio stimulus to optimize the effect on brain state, transforming the stimulus into the optimal audio stimulus. In additional embodiments, the system 100 can optimize multiple types of stimuli to be presented contemporaneously based on identified informative features for each type of stimulus (e.g., audio stimulus, visual stimulus, haptic stimulus, etc.). In other embodiments, the system 100 can optimize for multiple brains states. For example, the system 100 can maximize for focus and minimize for entrancement, etc.

The audio stimulus for brain state optimization may be used in a variety of contexts. In one or more contexts, the audio stimulus can be provided to digital music streaming platforms for use by their users to optimize brain state. In another context, the audio stimulus can be used in digital health. In still other contexts, the audio stimulus can be used in conjunction with other content (e.g., in a virtual reality (VR) environment, at a sporting event, in a movie theater, at a concert, etc.).

It is understood that the principles described in the method can be applied to different types of stimuli and various brain states. For example, the system 100 may optimize visual stimuli for a flow state. Additionally or alternatively, the system 100 can optimize other environmental stimuli (e.g., temperature, pressure, humidity, olfactory stimuli, touch stimuli, etc.) for achievement of a desired state of flow for a single user or a group of users (e.g., within an office environment).

3. Results

An example of the system, implementing methods described above, was used to generate the following results, with respect to generation and/or provision of were based on a study examining the effects of audio stimuli to affect states of flow/focus for individuals and groups of subjects. Sixty-two (62) participants (22 female), 18-65 years, completed four (4) sessions over a single (1) week at their own home. Adult participants were recruited from an opt-in screening panel and came from all five (5) major regions of the continental United States (Northeast, Southwest, West, Southeast, and Midwest). Only participants who reported normal hearing, normal vision, or vision that was corrected to normal with contact lenses were included. Volunteers who reported using medication that might influence the experiment or other neurological or psychiatric conditions that could influence the results were excluded. All participants were native English speakers; however, in other variations, other numbers of participants, from other demographics, characterized by other health states, and/or in other suitable environments can be implemented.

In the example, there was a sequence of 6 tasks prompted to each user: two user-selected tasks (i.e., a task that the user chose and performed in two intervals, amounting to two tasks), an arithmetic task, a creativity task, and two Tetris™ tasks. There were also 3 audio stimuli investigated: a playlist from Apple™ Music, a playlist from Spotify™, and a soundscape from Endel™, against the baseline of silence. EEG sensors were used to collect the brain activity, including two frontal channels, two temporal channels, and a reference channel, during calibration sessions, as well as during monitoring of states of flow (e.g., focus and enjoyment) and provision of stimuli to affect and improve states of flow.

Figure 4:
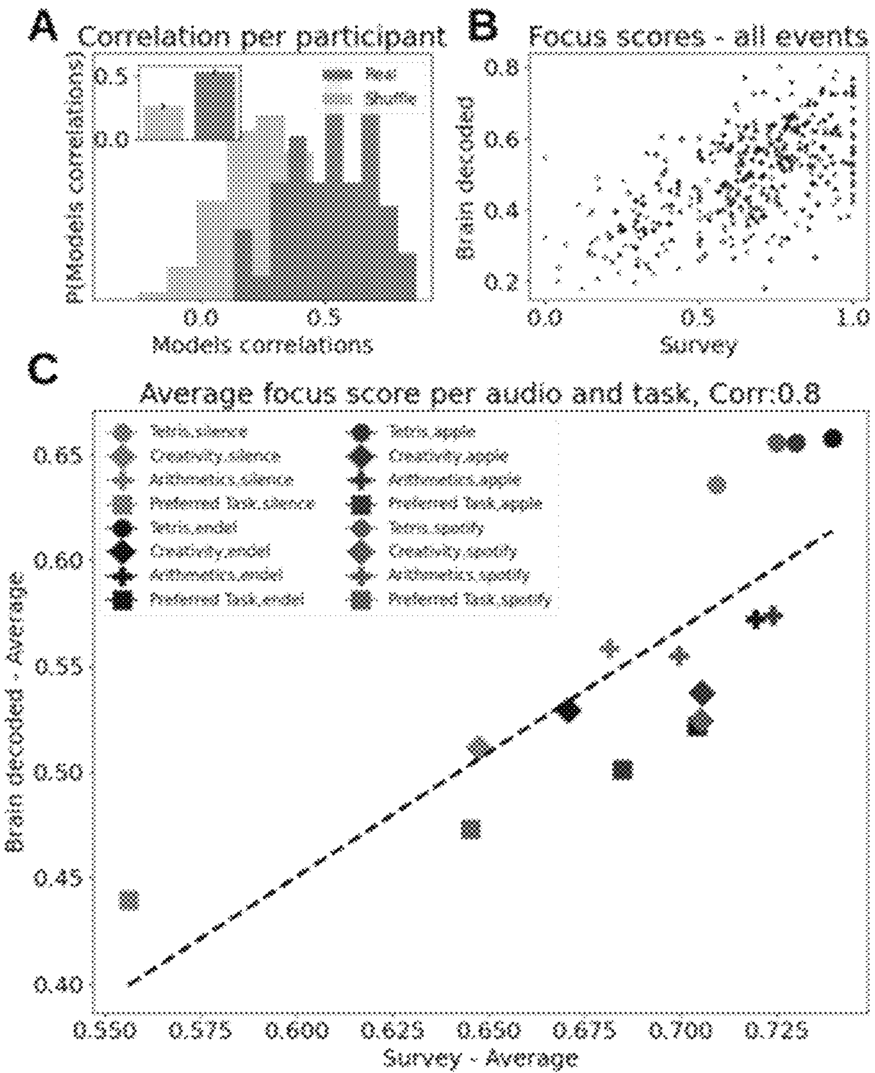
FIG. 4 illustrates graphs showing the predictive capabilities of the trained brain state models, in accordance with an exemplary implementation.

FIG. 4 illustrates graphs showing the predictive capabilities of the trained brain state models, in accordance with an exemplary implementation. The graphs relate to the effect of audio stimuli on a focus state. The graphs show the Pearson correlations between the model predictions (median across task) and the self-reported focus. Eleven (11) participants were excluded from the initial set to excessive noise in their recorded brain data and/or unreliable survey responses, leaving a total of 51 participants (mean age=36, SD=8, 17 females) in the experimental analysis. Average EEG features were calculated for all valid participants (N=51) in each subtask (e.g. creativity, tetris), resulting in 1224 focus ranked events (51 participants×4 sessions×6 ranked events per session). Then, in a cross-validation procedure, multiple random forests regression models were trained on random subsets of participants (80%) to predict the self-reported focus based on the EEG features. As such, the example system included architecture for training and refining model outputs, with respect to flow-associated parameters extracted from brain signal data, in coordination with task performance.

With respect to feature extraction from brain activity, from each EEG segment (epoch), relevant features were calculated: power spectrum features—each segment was transformed to the frequency domain using Welch method, and for each channel, the average power in different frequency bands was calculated. Power spectrum interactions—the power spectrum ratio between bands and engagement index. Time domain features—for each channel, the first four moments, entropy and number of zero-crossing points. Pairwise correlations between channels in the different frequency bands were calculated as well. For each epoch, a total of 124 features were extracted and to avoid extreme values, a programmatic trimming procedure was performed for high and low values.

Aggregating all tasks from all participants, the brain state models' performance is Corr(416)=0.6, p<10-4 (Graph B). The average correlation per participant is <Corr(24) >=0.543, p<10-4, while the average for the shuffled control is <Corr(24)>=0.26, p=0.34 (Graph A). Averaging the results across the tasks and the audio conditions, yielded a correlation of Corr(16)=0.8, p<5*10-4 (Graph C). Graph C also plots the average value of focus per audio stimulus and task. The relatively high correlations show the predictive power of the trained brain state models (in this case, focus models) to predict focus from brain activity data.

Figure 5:
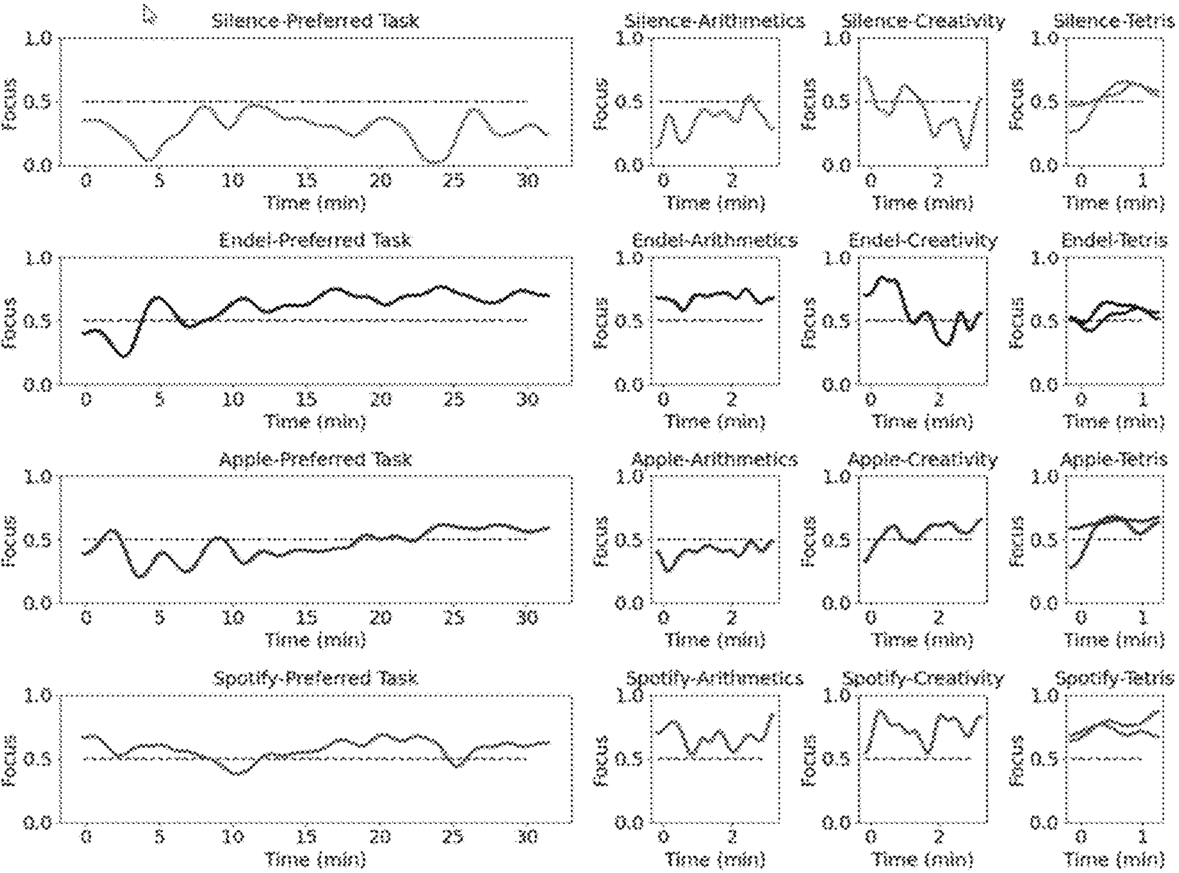
FIG. 5 illustrates predicted focus state of an individual with a trained focus model, in accordance with an exemplary implementation.

FIG. 5 illustrates predicted focus state of an individual with a trained focus model, in accordance with an exemplary implementation. The first row of graphs shows the predicted focus value over time as the user performed the tasks in silence, i.e., the control run. The second row of graphs shows the predicted focus value over time as the user performed the tasks with the Endel soundscape. The third row corresponds to the Apple™ playlist and the fourth row corresponds to the Spotify playlist. Across all the audio stimuli investigated, qualitatively, the audio stimuli was associated with a higher level of focus (e.g., focus, enjoyment) compared to the baseline silence.

Figure 6:
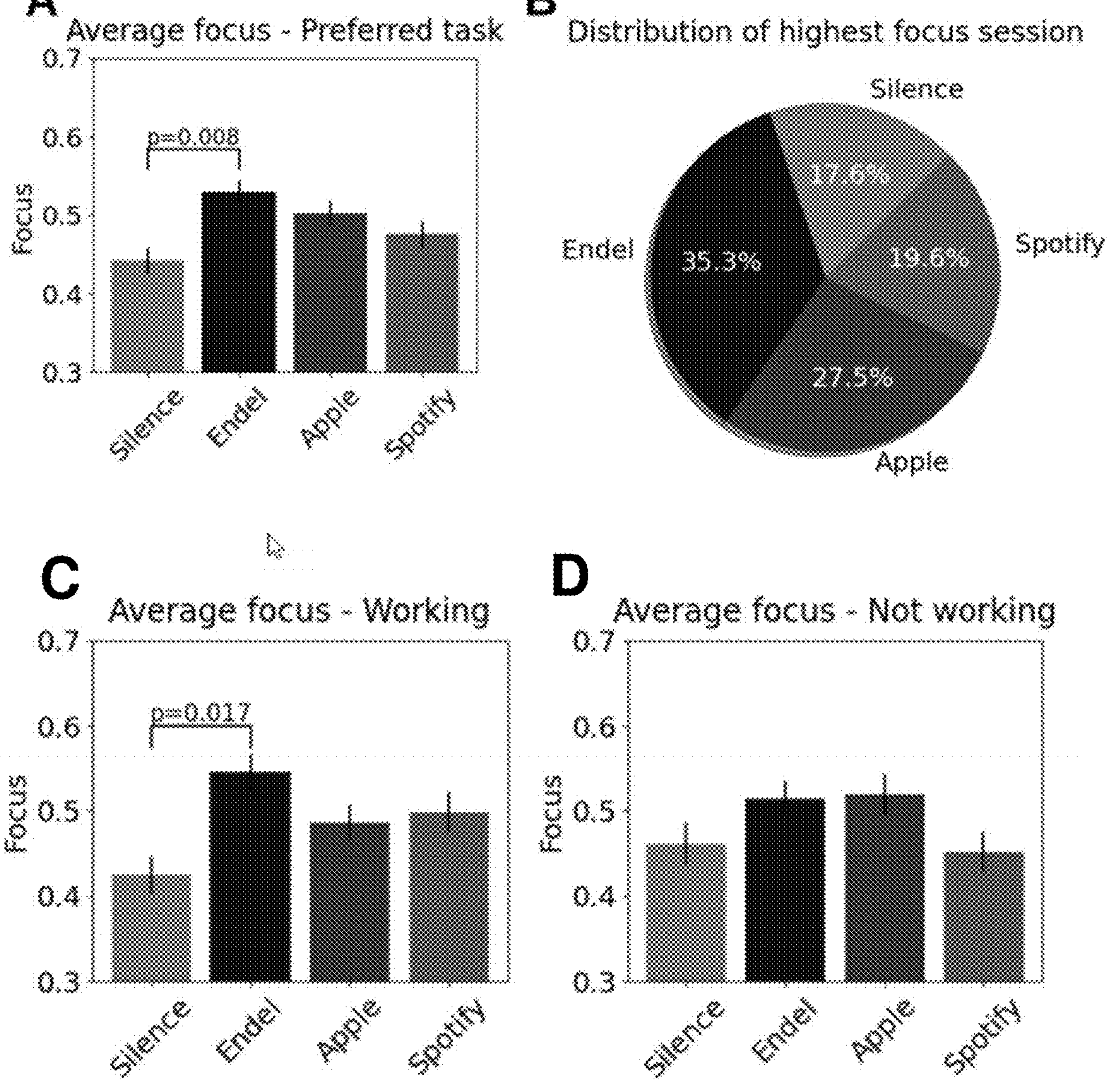
FIG. 6 illustrates graphs showing average focus for the preferred task, in accordance with an exemplary implementation.

FIG. 6 illustrates graphs showing average focus for the preferred task, in accordance with an exemplary implementation. Graph A shows the average focus for the user-selected task (or "Preferred task"). The 3 audio stimuli investigated had significant improved flow (e.g., focus, enjoyment) states compared to the silence control run. Graph B shows that among the participants, the Endel soundscape provided the highest focus session in a majority of the participants, followed by the Apple playlist then the Spotify playlist. Graphs C and D split participants who worked during the user-selected task versus those who chose another task ("Not working"). The two graphs show that the Endel soundscape provided significant increased flow (e.g., focus, enjoyment) for those working, with little difference between the other stimuli for those not working.

With the trained brain state models, the system 100 trained an audio-focus model to predict focus from the top audio features. The raw audio files of Apple and Spotify™ playlists were used to obtain audio features dynamics in the time and frequency domain. In this example, the features were calculated using Python's library pyAudioAnalysis57 (e.g. energy, spectral entropy, chroma coefficients). The features were calculated in audio epochs of 50 milliseconds with a sliding window of 25 milliseconds. Then, basic statistics of the audio features were calculated in windows of 30 seconds (e.g. mean and std), resulting in 136 features. To enable mapping to the brain model (e.g., brain model constructed and trained as described above), the brain decoded focus levels were also averaged in the corresponding 30 seconds windows. To map the relation between the calculated audio features and the averaged brain decoded focus, PCA was applied to reduce audio features dimensionality. The audio-focus model was trained as a regression model between the transformed audio features and the brain decoded focus (via cross-validation with 70% of the songs in each iteration) for the significant audio features only. The presented audio-focus model is a linear model based on the first PCA component of the features (shifted and rescaled).

Figure 7:
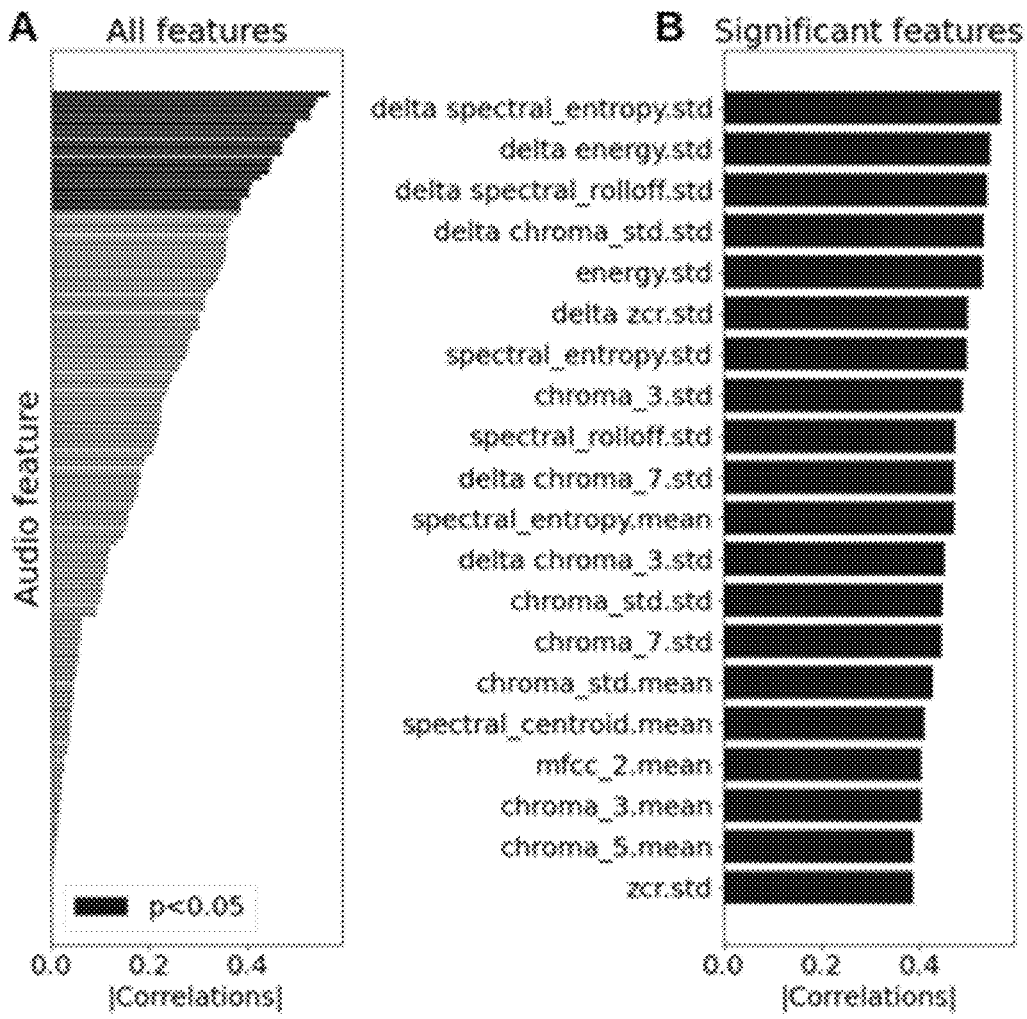
FIG. 7 illustrates the top audio features that contribute to focus, in accordance with an exemplary implementation.

FIG. 7 illustrates the top audio features that contribute to focus, in accordance with an exemplary implementation. Graph A shows the correlations for all extracted audio features. Significant audio features are colored and shown in Graph B, comprising only the top features with |Corr|>0.39.

Figure 8:
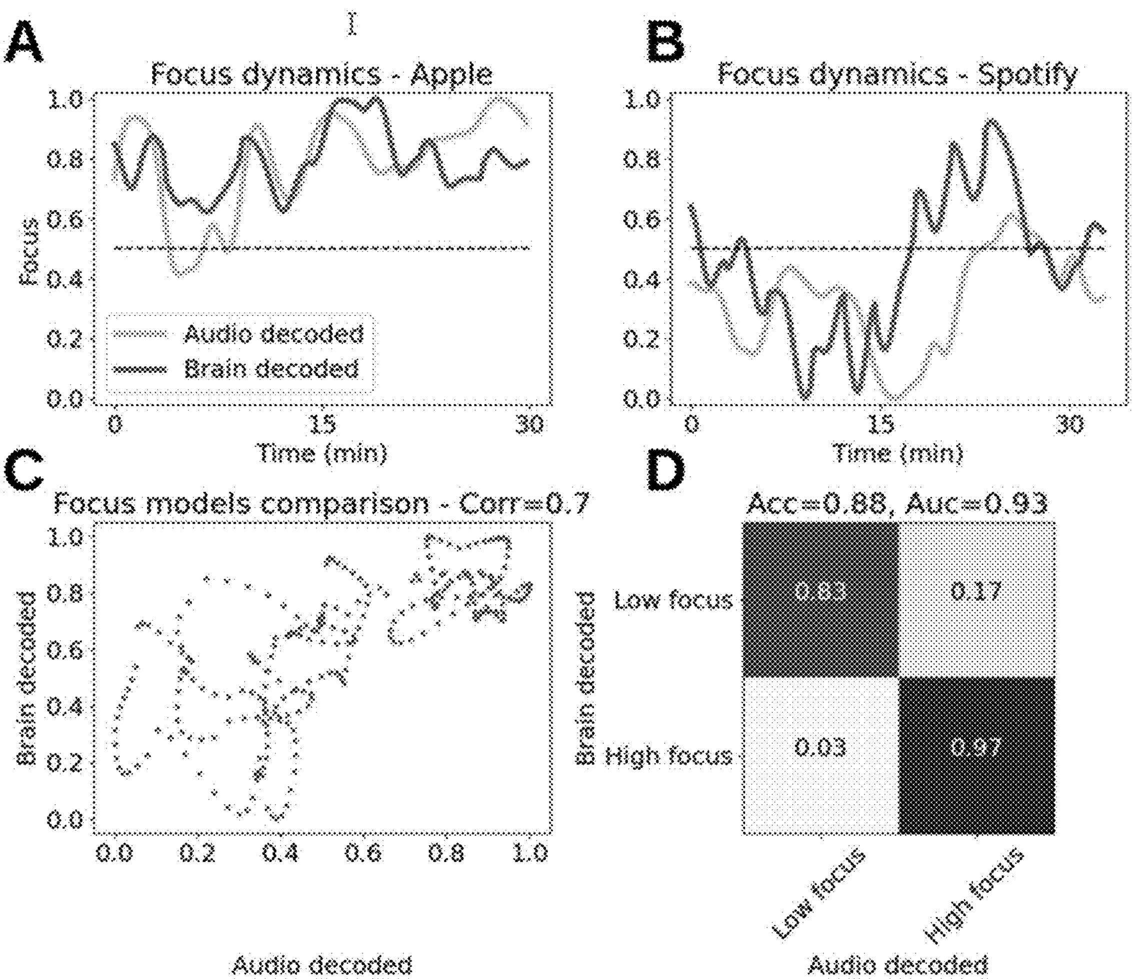
FIG. 8 illustrates graphs showing the predictive power of the audio-focus model, in accordance with an exemplary implementation.

FIG. 8 illustrates graphs showing the predictive power of the audio-focus model, in accordance with an exemplary implementation. Dynamics of brain decoded focus (from the focus models) and audio decoded focus (from the audio-focus model), during 30 minutes of the Preferred Task for the Apple playlist (Graph A) and the Spotify playlist (Graph B). Graph C shows brain decoded focus (y-axis) vs. audio decoded focus (x-axis) for both playlists (Apple and Spotify). Graph D shows a confusion matrix after thresholding the focus predictions to classify between low and high focus. Classification accuracy obtained: 88% (Area under ROC curve: 0.93).

Figure 9:
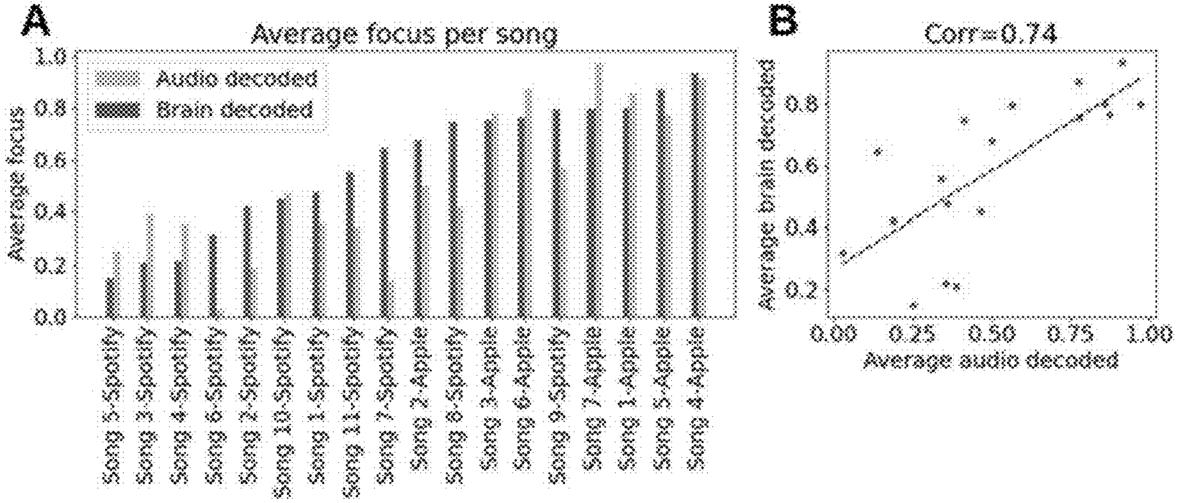
FIG. 9 illustrates graphs applying the audio-focus model to songs, in accordance with an exemplary implementation.

FIG. 9 illustrates graphs applying the audio-focus model to songs, in accordance with an exemplary implementation. Graph A shows sorted focus scores per song obtained by the focus models ("brain decoded"), next to the focus obtained by the audio-focus model ("audio decoded"). Graph B shows focus scores per song—brain decoded (y axis) vs. audio decoded (x axis). Pearson correlation between them: Corr(18)=0.74, p=0.0004.

4. Conclusion

The systems and methods described can confer benefits and/or technological improvements, several of which are described below.

The systems and methods can rapidly decode user brain activity states and dynamically generate customized digital objects and/or virtual environments with provision to users in near real time based the decoded brain activity states, with receipt of signals from brain computer interfaces. In particular the system includes architecture for rapidly decoding user states in a manner that can be used to provide digital content to the user in relation to dynamically changing user cognitive states. As such, the systems and methods can improve function of virtual reality, augmented reality, and/or brain computer interface devices relation to improved content delivery through devices that are subject to limitations in functionality.

The systems and methods can additionally efficiently process and deliver large quantities of data (e.g., neural signal data) by using a streamlined processing pipeline. Such operations can improve computational performance for data in a way that has not been previously achieved, and could never be performed efficiently by a human. Such operations can additionally improve function of a system for delivering digital content to a user, where enhancements to performance of the virtual system provide improved functionality and application features to users of the virtual system.

Furthermore, the systems and methods generate novel user identification objects, based on reinforced versions of digital objects tuned to neurological signatures of the user. Such novel objects serve as neurobiometric elements that can be used to differentiate identities of different users in a way that has not been achieved before.

The foregoing description of the embodiments has been presented for the purpose of illustration; it is not intended to be exhaustive or to limit the patent rights to the precise forms disclosed. Persons skilled in the relevant art can appreciate that many modifications and variations are possible in light of the above disclosure.

Some portions of this description describe the embodiments in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product comprising a computer-readable medium containing computer program code, which can be executed by a computer processor for performing any or all of the steps, operations, or processes described. The computer can be a specialized computer designed for user with a virtual environment.

Embodiments may also relate to an apparatus for performing the operations herein. This apparatus may be specially constructed for the required purposes, and/or it may comprise a general-purpose computing device selectively activated or reconfigured by a computer program stored in the computer. Such a computer program may be stored in a non-transitory, tangible computer readable storage medium, or any type of media suitable for storing electronic instructions, which may be coupled to a computer system bus. Furthermore, any computing systems referred to in the specification may include a single processor or may be architectures employing multiple processor designs for increased computing capability.

Embodiments may also relate to a product that is produced by a computing process described herein. Such a product may comprise information resulting from a computing process, where the information is stored on a non-transitory, tangible computer readable storage medium and may include any embodiment of a computer program product or other data combination described herein.

Finally, the language used in the specification has been principally selected for readability and instructional purposes, and it may not have been selected to delineate or circumscribe the patent rights. It is therefore intended that the scope of the patent rights be limited not by this detailed description, but rather by any claims that issue on an application based hereon. Accordingly, the disclosure of the embodiments is intended to be illustrative, but not limiting, of the scope of the patent rights, which is set forth in the following claims.

What is claimed is:

1. A method for brain state optimization, the method comprising:

prompting a set of users to perform a sequence of tasks in coordination with provision of a stimulus;

recording a brain activity signal for each user of the set of users while the user is performing the sequence of tasks;

receiving a reported brain state value, reported by each user of the set of users, for each task of the sequence of tasks;

training a first brain state model based on the brain activity signals recorded from the set of users and the reported brain state values, wherein the first brain state model is configured to process an input brain activity signal and to output a predicted brain state value based on the input brain activity signal;

applying the first brain state model to predict a first brain state value for each user and each task;

extracting a set of features from the stimulus;

training a stimulus-brain model based on the set of features and the first brain state values over the set of users and the sequence of tasks; and generating an optimal stimulus to achieve a target brain state value based on the trained stimulus-brain model.

2. The method of claim 1, wherein the sequence of tasks includes a first task from a first category of tasks and a second task from a second category of tasks different from the first category.

3. The method of claim 1, wherein the brain activity signal recorded for each user of the set of users comprises a plurality of electroencephalogram (EEG) channels.

4. The method of claim 1, further comprising:

partitioning the brain activity signals for the set of users into brain activity epochs using a sliding window; and featurizing the brain activity epochs, wherein the brain state model is trained on the features for the brain activity epochs.

5. The method of claim 1, wherein the first brain state model is one of: a regression model, a neural network, a random forest model, and a decision tree model.

6. The method of claim 1, wherein the first brain state model is trained on the brain activity signals from a random subset of users from the set of users.

7. The method of claim 6, further comprising:

training a second brain state model based on the brain activity signals from a second random subset of users from the set of users, wherein the second brain state model is configured to input a brain activity signal and to output a predicted brain state value based on the input brain activity signal;

for each user and each task, applying the second brain state model to the brain activity signal to predict a second brain state value; and wherein training of the stimulus-brain model is further based on the second brain state values over the set of users and the sequence of tasks.

8. The method of claim 7, further comprising:

for each user, selecting between the first brain state values and the second brain state values that are closest to the reported brain state values over the sequence of tasks for the user; and wherein the training of the stimulus-brain model is based on the selection.

9. The method of claim 1, wherein extracting the set of features from the stimulus comprises:

partitioning an audio stimulus into audio epochs using a second sliding window; and extracting the set of features for each of the audio epochs.

10. The method of claim 1, further comprising:

prompting the set of users to reperform the sequence of tasks in coordination with provision of a second stimulus;

wherein recording the brain activity signals comprises recording while the set of users are reperforming the sequence of tasks in coordination with the second stimulus, and wherein the set of features is also extracted from the second stimulus, for training of the stimulus-brain model.

11. The method of claim 1, wherein generating the optimal stimulus further comprises optimizing for a second brain state.

* * * * *